(12) United States Patent
Albagli et al.

(10) Patent No.: US 6,621,887 B2
(45) Date of Patent: Sep. 16, 2003

(54) METHOD AND APPARATUS FOR PROCESSING A FLUOROSCOPIC IMAGE

(75) Inventors: Douglas Albagli, Clifton Park, NY (US); Brian David Yanoff, Schenectady, NY (US); John Eric Tkaczyk, Delanson, NY (US); George Edward Possin, Niskayuna, NY (US); Ping Xue, Cottage Grove, WI (US)

(73) Assignee: General Electric Company, Schenectady, NY (US)

( * ) Notice: Subject to any disclaimer, the term of this patent is extended or adjusted under 35 U.S.C. 154(b) by 121 days.

(21) Appl. No.: 09/977,474

(22) Filed: Oct. 15, 2001

(65) Prior Publication Data

US 2003/0072418 A1 Apr. 17, 2003

(51) Int. Cl.$^7$ ................................................. G03C 9/00
(52) U.S. Cl. ..................... 378/42; 378/98.11; 250/208.1
(58) Field of Search ............................ 378/19, 210, 42, 378/44, 62, 98.8, 98.11, 98.12, 207, 98.91; 250/208.1; 382/128, 131, 132

(56) References Cited

U.S. PATENT DOCUMENTS

| | | | |
|---|---|---|---|
| 4,482,918 A | 11/1984 | Keyes et al. | |
| 4,752,944 A | 6/1988 | Conrads et al. | |
| 4,975,935 A | 12/1990 | Hillen et al. | |
| 5,272,536 A | 12/1993 | Sudo et al. | |
| 5,493,598 A * | 2/1996 | Yassa et al. | 378/98.2 |
| 5,563,421 A | 10/1996 | Lee et al. | |
| 5,608,205 A * | 3/1997 | Bird et al. | 250/208.1 |
| 5,969,360 A | 10/1999 | Lee | |
| 5,999,587 A * | 12/1999 | Ning et al. | 378/4 |
| 6,084,936 A * | 7/2000 | Patch | 378/4 |
| 6,404,853 B1 * | 6/2002 | Odogba et al. | 378/98.8 |

\* cited by examiner

Primary Examiner—Drew A. Dunn
Assistant Examiner—Irakli Kiknadze
(74) Attorney, Agent, or Firm—Armstrong Teasdale LLP; Robert B. Reeser, III

(57) ABSTRACT

In one aspect of the invention a method for processing a fluoroscopic image is provided. The method includes scanning an object with an imaging system including at least one radiation source and at least one detector array, acquiring a plurality of dark images to generate a baseline image, acquiring a plurality of lag images subsequent to the baseline image, determining a plurality of parameters of a power law using at least one lag image and at least one baseline image, and performing a log—log extrapolation of the power law including the determined parameters.

21 Claims, 5 Drawing Sheets

METHOD AND APPARATUS FOR PROCESSING A FLUOROSCOPIC IMAGE

BACKGROUND OF THE INVENTION

This invention relates generally to imaging systems and more particularly to a method and apparatus for processing a fluoroscopic image.

In at least some known imaging systems, a radiation source projects a cone-shaped beam which passes through the object being imaged, such as a patient and impinges upon a rectangular array of radiation detectors.

In some known radiation detectors, such as those including thin film transistors (TFTs) and photodiodes, a "lag" signal may occur. Lag is a dependence of an image signal due to the past exposure history. Some known medical applications require a transition from high radiation exposure to fluoroscopic mode, which uses low exposure. A lag signal from the high exposure may introduce artifacts into the fluoroscopic images in the form of ghost images of the high exposure image.

BRIEF DESCRIPTION OF THE INVENTION

In one aspect of the invention a method for processing a fluoroscopic image is provided. The method includes scanning an object with an imaging system including at least one radiation source and at least one detector array, acquiring a plurality of dark images to generate a baseline image, acquiring a plurality of lag images subsequent to the baseline image, determining a plurality of parameters of a power law using at least one lag image and at least one baseline image, and performing a log—log extrapolation of the power law including the determined parameters.

In another aspect, a medical imaging system for processing a fluoroscopic image that includes a detector array, at least one radiation source, and a computer coupled to the detector array and the radiation source is provided. The computer is configured instruct the medical imaging system to scan an object, acquire a plurality of dark images to generate a baseline image, acquire a plurality of lag images subsequent to the baseline image, determine a plurality of parameters of a power law using at least one lag image and at least one baseline image, and perform a log—log extrapolation of the power law including the determined parameters.

In yet another aspect, a computer readable medium encoded with a program executable by a computer for processing a fluoroscopic image is provided. The program is configured to instruct the computer to scan an object with an imaging system, acquire a plurality of dark images to generate a baseline image, acquire a plurality of lag images subsequent to the baseline image, determine a plurality of parameters of a power law using at least one lag image and the baseline image, and perform a log—log extrapolation of the power law including the determined parameters.

In yet a further aspect of the invention, a method for processing a fluoroscopic image is provided. The method includes scanning an object with an imaging system including at least one radiation source and at least one detector array, acquiring a plurality of dark images to generate a baseline image, acquiring at least one first radiation image subsequent to the baseline image, acquiring a second dark image subsequent to the first radiation image, and acquiring a second radiation image subsequent to the second dark image. The method also includes generating a lag prediction image by subtracting the baseline image from the second dark image and subtracting the lag prediction image from at least one subsequent radiation image to generate at least one lag-corrected fluoroscopic image.

In still another further aspect of the invention, a method for processing a fluoroscopic image is provided. The method includes scanning an object with an imaging system including at least one radiation source and at least one detector array. The method further includes generating a baseline image, acquiring at least one radiation image subsequent to the dark image, processing a fluoroscopic image after acquiring a dark image every $n^{th}$ frame, and acquiring a dark image every $n^{th}$ frame, where $n>1$.

DETAILED DESCRIPTION OF THE INVENTION

Figure 1:
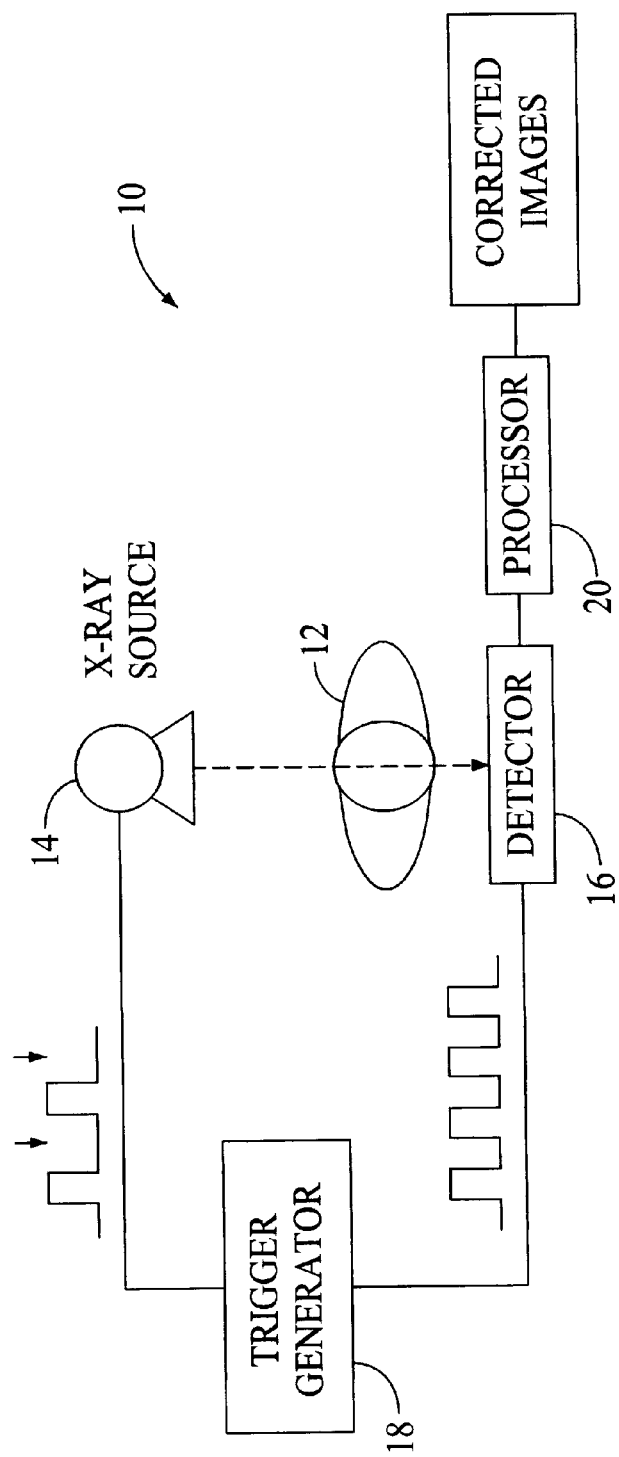
FIG. 1 is a pictorial view of an imaging system.

Referring to FIG. 1, and in an exemplary embodiment, a digital imaging system 10 generates a plurality of two dimensional images representative of an imaged object 12, such as, but not limited to, performing diagnosis of an object of interest, e.g., a patient's heart in cardiac fluoroscopy. System 10 includes a radiation source 14, such as an x-ray source 14, and at least one detector array 16 for collecting projection data. Specifically and in one embodiment, system 10 includes a radiation source 14 which projects a cone-shaped beam of x-rays which pass through object 12 and impinge on detector array 16. Detector array 16 is fabricated in a panel configuration having a plurality of pixels (not shown) arranged in rows and columns so that an image is generated for an entire object of interest such as heart 12. Each pixel includes a photosensor, such as a photodiode, that is coupled via a switching transistor to two separate address lines, a scan line and a data line. The radiation incident on a scintillator material and the pixel photosensors measure, by way of change in the charge across the diode, the amount of light generated by x-ray interaction with the scintillator. As a result, each pixel produces an electric signal that represents the intensity, after attenuation by object 12, of an x-ray beam impinging on detector array 16.

The operation of radiation source 14 is controlled by a computer 18. Computer 18 provides power and timing signals to radiation source 14 and detector 16. In one embodiment, computer 18 includes an image processor 20. Alternatively, computer 18 and processor 20 can be separate components. Image processor 20 receives sampled and digitized radiation data from detector 16 and performs high-speed image processing, as described herein. The processed two-dimensional image, representative of imaged object 12, is applied as an input to a computer 18. Computer 18 is programmed to perform functions described herein, and, as used herein, the term computer refers to microcontrollers, microcomputers, programmable logic controllers, application specific integrated circuits, and other programmable circuits.

In use, a patient is positioned so that the object of interest 12 is within the field of view of system 10, i.e., heart 12 is positioned within the imaged volume extending between radiation source 14 and detector array 16. Images of heart 12 are then acquired to generate a plurality of radiographic images or fluoroscopic images of the volume of interest.

Figure 2:
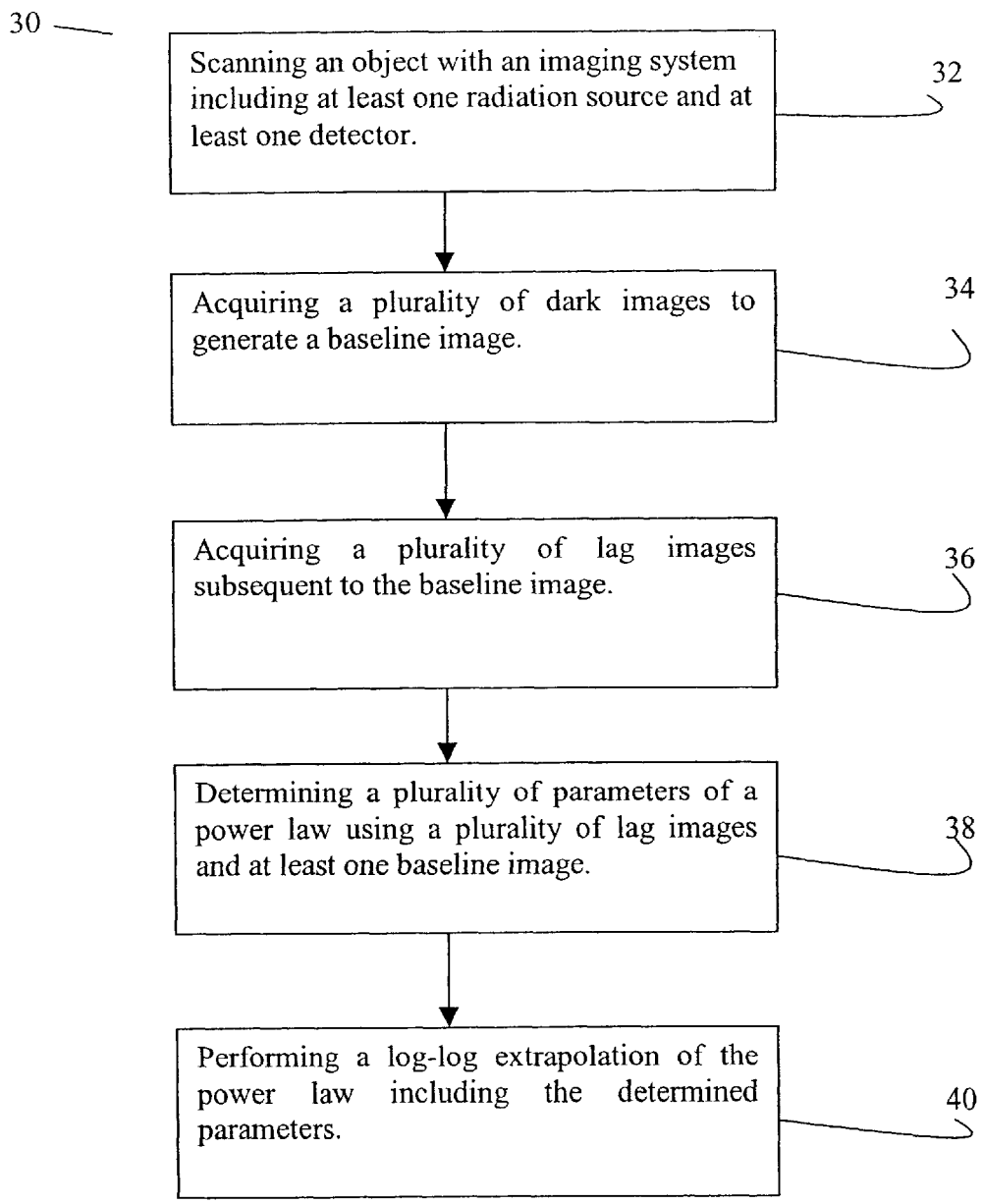
FIG. 2 is a flow diagram of a method for processing a fluoroscopic image.

FIG. 2 is a flow diagram illustrating a method 30 which includes scanning 32 an object 12 (shown in FIG. 1) with an imaging system 10 (shown in FIG. 1) including at least one radiation source 14 (shown in FIG. 1) and at least one detector array 16 (shown in FIG. 1).

In one embodiment, scanning 32 object 12 includes acquiring 34 a plurality of dark images. Acquiring 32 a dark or offset image in the absence of x-ray and light represents a dark scan, and results in a signal that is slightly negative. This negative charge is "retained" by a photodiode in a detector array, such as detector array 16 (shown in FIG. 1), when it is initiated or scanned. Retained charges "leak out" slowly over time and add a positive signal to pixels that are read subsequently. In use, a plurality of dark scans are performed to acquire 34 a plurality of dark images. The plurality of dark images are averaged together to generate a baseline image.

In one embodiment, a higher order prediction of lag can be acquired using a power law. In use, a plurality of lag images are acquired 36 subsequent to the baseline image. The baseline image is subtracted from a plurality of lag images acquired 36 subsequent to the base line image. A plurality of lag images and at least one baseline image are used to determine 38 a plurality of parameters of a power law. Power law as used herein refers to a single term function, $f(x)=x^m+c$, where dependent variable x has an exponent, i.e. x is raised to some power m, and includes a constant c. Method 30 also includes performing 40 a log—log extrapolation of the power law including the determined parameters.

Figure 3:
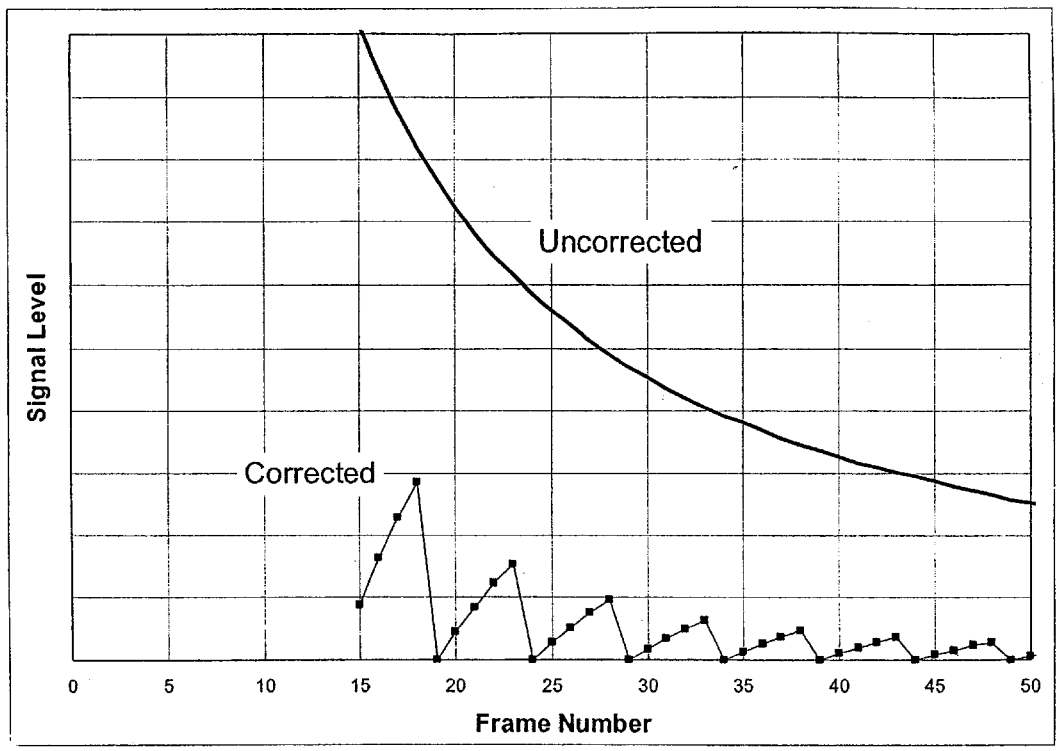
FIG. 3 is a graphical representation of an exemplary embodiment of the method described in FIG. 2.

FIG. 3 is a graphical representation of an exemplary embodiment of the method described in FIG. 2. In one embodiment, a log—log extrapolation of two lag images is performed to extrapolate an approximate power law time dependence for each pixel. Power law time dependence results in a straight line on such a log—log plot, such that this extrapolation technique is effective to the degree that the lag follows a power law. Because the slope and intercept are calculated individually for each pixel, the correction is indifferent to variations in the exponent of the power law from pixel to pixel, such as result from variations in the exposure over the image.

Alternatively, the log—log extrapolation of more than two lag images is performed to extrapolate approximate power law time dependence. A log—log extrapolation can be used to predict lag at future frames and this prediction subtracted to yield a corrected signal. For example, and referring to FIG. 3, every fifth radiation pulse is dropped and a dark image is acquired, i.e. frames nineteen and twenty-four are dark and frames twenty through twenty-three are illuminated. Dark frames nineteen and twenty-four can be used to extrapolate the lag to frames twenty-five through twenty-eight and correct them. This process can continue with each successive pair of dark frames used to extrapolate to the subsequent illuminated frames. Because each extrapolation extends only a short time into the future, the dark frames are less sensitive to noise. Alternatively any quantity of illuminated frames can be dropped.

In one embodiment, The logarithms can be pre-calculated and implemented as a look-up table, and the two-point linear interpolation (of the logs) is a simple formula. Because each pixel is corrected individually, the variation of the power law exponent with signal level is not a problem.

Figure 4:
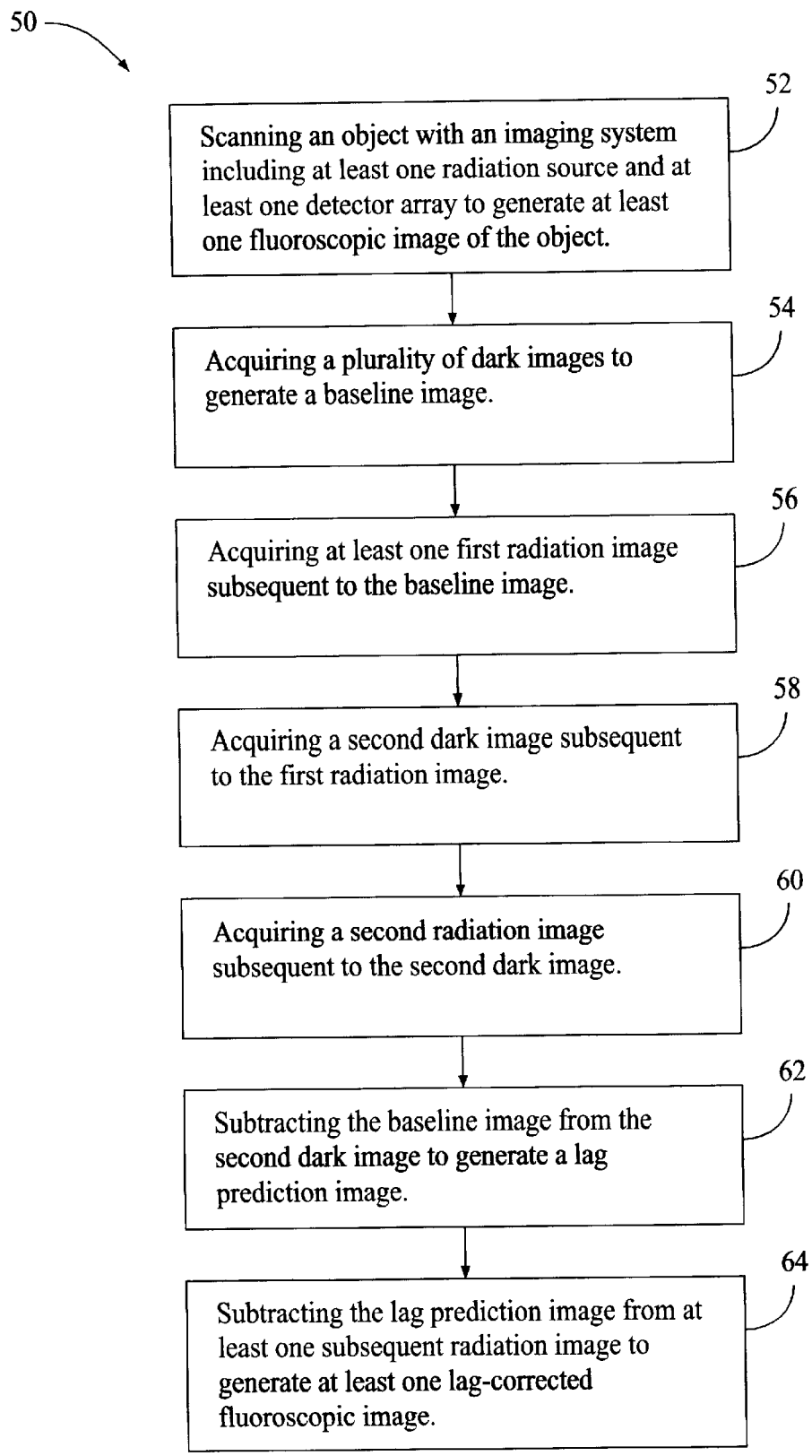
FIG. 4 is flow diagram of an alternative method for processing a fluoroscopic image.

In one embodiment, a low-pass spatial filter, such as, but not limited to a boxcar, is applied to the lag image prior to subtracting the lag image from the radiation image to generate the lag-corrected image with a reduced number of artifacts. In another embodiment, a more sophisticated low-pass filter may be used. For example, if a lag image is subtracted from a subsequent radiation image which includes some amount of noise, the noise in the lag-corrected image is the quadrature sum of the noise of the individual images. In the lowest order correction strategy, the lag image, which contains electronic noise $N_e$ is subtracted from the radiation image which contains quantum noise $N_Q$, and electronic noise $N_e$. The effective electronic noise in the difference image is increased by a factor of sqrt2, while the quantum noise remains the same. For typical exposure conditions, using a typical x-ray to electron conversion factor, this results in an increase of approximately 5% in the lag-corrected image noise. The low-pass filter facilitates a reduction in noise for both the simple subtraction strategy and the higher order correction strategy. Alternatively, the low-pass filter is not used. In one embodiment, multi-point extrapolation can be used to facilitate a reduction in noise in a subsequent lag image FIG. 4 is a flow diagram of an alternative method 50 for processing a fluoroscopic image. Method 50 includes scanning 52 an object 12 (shown in FIG. 1) with an imaging system 10 (shown in FIG. 1) including at least one radiation source 14 (shown in FIG. 1) and at least one detector array 16 (shown in FIG. 1).

In one embodiment, scanning 52 object 12 includes generating a fluoroscopic sequence of frames. The fluoroscopic sequence of frames includes at least one frame that is generated by exposing object 12 to radiation (radiation image), and at least one frame that is generated by a dark scan (dark image). In one embodiment, the dark scan is performed every n frame of the fluoroscopic sequence to generate at least one dark image.

In use, a plurality of dark scans are performed to acquire 54 a plurality of dark images. The plurality of acquired 54 dark images are averaged together to generate a baseline image. At least one first radiation image is acquired 56 subsequent to the baseline image. A second dark image, subsequent to the first radiation image is then acquired 58. A second radiation image is acquired 60 subsequent to the second dark image. In one embodiment, the baseline image is subtracted 62 from at least one subsequent dark image to generate a lag image. The lag image defines a lag signal for each pixel in that frame. Alternatively, a plurality of lag images is combined to generate the lag prediction image, i.e. a lag predicted in future frames. The lag prediction image is subtracted 64 from at least one subsequent radiation image in the fluoroscopic sequence to generate at least one lag-corrected fluoroscopic image.

In one embodiment, a dark image is acquired every $n^{th}$ frame. For example, if n=2, the fluoroscopic sequence includes a dark scan that is followed by a radiation scan throughout a scan process. Alternating a dark scan with a radiation scan facilitates increasing the number of lag measurements, reduces a panel readout frame rate by one-half, and reduces a radiation dosage to the object by approximately one-half. Alternatively, an operator can double the radiation dosage by doubling the amplitude of each of the remaining fluoroscopic pulses. During use, the power of the radiation source, and the patient dosage are returned to their original values. The increase in dosage facilitates improved image quality by increasing the signal-to-noise ratio by approximately 22%. Additionally, because the human visual system acts as a low pass temporal filter, the relationship between image quality and signal-to-noise ratio is not strictly linear. Therefore, the radiation dosage can be reduced to a level less than twice the normal dosage without affecting image quality.

In use, fluoroscopic frames are numbered sequentially beginning with the first frame read after radiation exposure, and a slope and intercept of the logarithm of the lag signal versus the logarithm of the frame number are calculated for at least one pixel. Alternatively, the slope and intercept of the logarithm of the lag signal versus the logarithm of the frame number are calculated for each pixel. For each subsequent frame, another lag image is generated and is then subtracted from the base image to generate 62 a new lag prediction image. The new lag prediction image is then subtracted 64 from the next fluoroscopic image in the sequence to generate a lag-corrected fluoroscopic image.

In one embodiment, a least-squares fit to the pre-fluoroscopic frames can be used instead of taking just two points. The least-squares fit of the pre-fluoroscopic frames facilitates a reduction in the sensitivity to noise. In another alternative embodiment, a low-pass spatial filter, such as, but not limited to a boxcar, can be used.

In another embodiment, generating 62 a lag prediction in at least one fluoroscopic image includes predicting lag using a higher order operator that is a polynomial. Polynomial as used herein refers to a multiple term function, where at least one term, $f(x^p)$, has a dependent variable x, wherein x has an exponent, i.e. x is raised to some power p. Using a polynomial facilitates predicting lag when real-time image processing power is available, or if the image processing is not executed in real time, the polynomial can be used for the log—log fit to account for the inexact power law dependence. A polynomial of order P requires P+1 lag images for a fully constrained fit.

In a further embodiment, generating 62 a lag prediction in at least one fluoroscopic image includes predicting lag using a constant offset value for each pixel. In use, the lag prediction image is loaded into a buffer. The lag prediction image is subtracted 64 from the next N−1 frames in the fluoroscopic sequence. The error in the lag prediction image, and therefore, the visibility of the lag artifact, increases with each subsequent frame until a new lag prediction image is generated 62. However, if N=2, then the lag prediction image is subtracted 64 from the next frame only and generates a lag-corrected image with a reduced number of artifacts. Therefore, setting N=2 eliminates the above mentioned error growth. A new lag prediction image is then generated 62 and loaded into the buffer and the process repeated.

Figure 5:
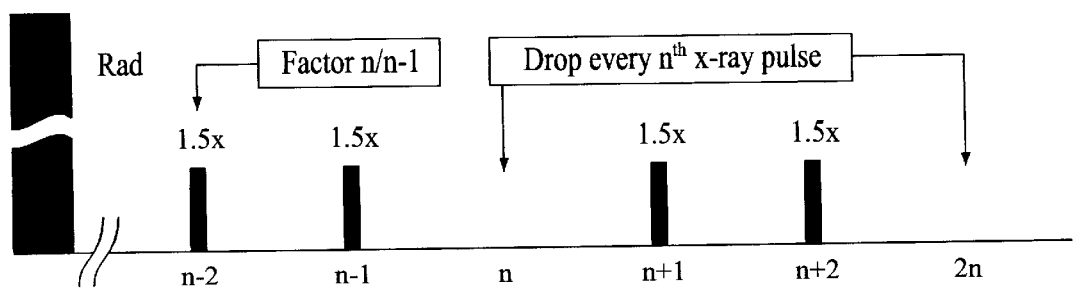
FIG. 5 is a schematic representation of an exemplary embodiment of the alternative method described in FIG. 4.

FIG. 5 is a schematic representation of an exemplary embodiment of the method described in FIG. 4. For n=3, every third fluoroscopic pulse is dropped and a dark scan is performed. The lag decreases with time, and as such, the lag at frame i is always larger than the lag at frame i+1, i+2 . . . i+n. As a result, the residual signal, after subtraction, will appear as a negative ghost image. A top line shown in FIG. 5 illustrates and exemplary embodiment where every third fluoroscopic pulse is dropped and a dark scan is performed. The pixel values of these dark frames are carried forward and subtracted from two subsequent frames. Additionally, the radiation dosage can be increased by a factor of 1.5 by increasing the amplitude of each of the remaining fluoroscopic pulses by a factor of 1.5. In general, a radiation dosage factor is n/n−1.

In another exemplary embodiment, a method for processing a fluoroscopic image is provided. The method includes scanning an object wit an imaging system including at least one radiation source and at least one detector array. The method further includes generating a baseline image, acquiring at least one radiation image subsequent to the dark image and acquiring a dark image every $n^{th}$ frame, processing a fluoroscopic image after acquiring a dark image every $n^{th}$ frame, and acquiring a dark image every $m^{th}$ frame, where m>n.

While the invention has been described in terms of various specific embodiments, those skilled in the art will recognize that the invention can be practiced with modification within the spirit and scope of the claims.

What is claimed is:

1. A method for processing a fluoroscopic image, said method comprising:
   scanning an object with an imaging system including at least one radiation source and at least one detector array;
   acquiring a plurality of dark images to generate a baseline image;
   acquiring a plurality of lag images subsequent to the baseline image;
   determining a plurality of parameters of a power law using at least one lag image and at least one baseline image;
   performing a log—log extrapolation of the power law including the determined parameters.

2. A method in accordance with claim 1 wherein acquiring a plurality of dark images to generate a baseline comprises averaging the plurality of dark images to generate at least one baseline image.

3. A method in accordance with claim 1 further comprises subtracting the log—log extrapolation value from at least one fluoroscopic image to generate a lag-corrected fluoroscopic image.

4. A method in accordance with claim 3 wherein the log—log extrapolation is spatially filtered prior to subtraction.

5. A method for processing a fluoroscopic image comprising:
   scanning an object with an imaging system including at least one radiation source and at least one detector ray;
   acquiring a plurality of dark images;
   generating at least one baseline image using at least one dark image;
   acquiring a plurality of lag images subsequent to the baseline image;
   determining a plurality of parameters of a power law using at least one lag image and at least one baseline image;
   performing a log—log extrapolation of the power law including the determined parameters;
   spatially filtering the log—log extrapolation; and
   subtracting the log—log extrapolation value from at least one fluoroscopic image to generate a lag-corrected fluoroscopic image.

6. A medical imaging system for processing a fluoroscopic image, said medical system comprising:
   a detector array;
   at least one radiation source; and
   a computer coupled to said detector array and said radiation source, said computer configured to:
   scan an object;
   acquire a plurality of dark images to generate a baseline image;

acquire a plurality of lag images subsequent to the baseline image;

determine a plurality of parameters of a power law using at least one lag image and at least one baseline image;

perform a log—log extrapolation of the power law including the determined parameters.

7. A medical imaging system in accordance with claim 6, wherein to acquire a plurality of dark images to generate a baseline, said computer is further configured to average the plurality of dark images to generate at least one baseline image.

8. A medical imaging system in accordance with claim 6 wherein to process a fluoroscopic image, said computer is further configured to subtract the log—log extrapolation value from at least one fluoroscopic image to generate a lag-corrected fluoroscopic image.

9. A medical imaging system in accordance with claim 8 wherein said computer is further configured to spatially filter the log—log extrapolation prior to subtraction.

10. A medical imaging system for processing a fluoroscopic image, said medical system comprising:

a detector array;

at least one radiation source; and a computer coupled to said detector array and said radiation source, said computer configured to:

acquire a plurality of dark images;

generate at least one baseline image using at least one dark image;

acquire a plurality of lag images subsequent to the baseline image;

determine a plurality of parameters of a power law using at least one lag image and at least one baseline image;

perform a log—log extrapolation of the power law including the determined parameters;

filter the log—log extrapolation spatially; and subtract the log—log extrapolation value from at least one fluoroscopic image to generate a lag-corrected fluoroscopic image.

11. A computer readable medium encoded with a program executable by a computer for processing a fluoroscopic image, said program configured to instruct the computer to:

scan an object with an imaging system including at least one radiation source and at least one detector array;

acquire a plurality of dark images to generate a baseline image;

acquire a plurality of lag images subsequent to the baseline image;

determine a plurality of parameters of a power law using at least one lag image and the baseline image;

perform a log—log extrapolation of the power law including the determined parameters.

12. A computer readable medium in accordance with claim 11 wherein to process a fluoroscopic image, said program configured to average the plurality of dark images to generate at least one baseline image.

13. A computer readable medium in accordance with claim 11 wherein to process a fluoroscopic image, said program configured to subtract the log—log extrapolation value from at least one fluoroscopic image to generate a lag-corrected fluoroscopic image.

14. A computer readable medium in accordance with claim 13, said program configured to spatially filter the log—log extrapolation prior to subtraction.

15. A computer readable medium encoded with a program executable by a computer for processing a fluoroscopic image, said program configured to instruct the computer to:

scan an object wit an imaging system including at least one radiation source and at least one detector array;

acquire a plurality of dark images;

generate at least one baseline image using at least one dark image;

acquire a plurality of lag images subsequent to the baseline image;

determine a plurality of parameters of a power law wing at least one lag image and at least one baseline image;

perform a log—log extrapolation of the power law including the determined parameters;

filter the log—log extrapolation spatially; and subtract the log—log extrapolation value from at least one fluoroscopic image to generate a lag-corrected fluoroscopic image.

16. A method for processing a fluoroscopic image comprising:

scanning an object with an imaging system including at least one radiation source and at least one detector array;

acquiring a plurality of dark images to generate a baseline image;

acquiring at least one first radiation image subsequent to the baseline image;

acquiring a second dark image subsequent to the first radiation image;

acquiring a second radiation image subsequent to the second dark image;

generating a lag prediction image by subtracting the baseline image from the second dark image; and subtracting the lag prediction image from at least one subsequent radiation image to generate at least one lag-corrected fluoroscopic image.

17. A method in accordance with claim 16 wherein generating at least one lag prediction image comprises generating at least one lag prediction image using a constant offset value.

18. A method in accordance with claim 16 wherein generating at least one lag prediction image comprises generating at least one lag prediction image using a polynomial.

19. A method in accordance with claim 16 wherein subtracting the lag prediction image from at least one radiation image to generate at least one lag-corrected image comprises filtering the lag prediction image prior to subtraction.

20. A method for processing a fluoroscopic image comprising:

scanning an object with an imaging system including at least one radiation source and at least one detector array;

generating a baseline image;

acquiring at least one radiation image subsequent to the dark image; and acquiring a dark image every $n^{th}$ frame;

processing a fluoroscopic image after acquiring a dark image every $n^{th}$ frame; and acquiring a dark image every $m^{th}$ frame, where m>n.

21. A method in accordance with claim 20 wherein acquiring a dark image every $n^{th}$ frame includes filtering the lag prediction image.

* * * * *

UNITED STATES PATENT AND TRADEMARK OFFICE
CERTIFICATE OF CORRECTION

PATENT NO. : 6,621,887 B2
DATED : September 16, 2003
INVENTOR(S) : Douglas Albagli et al.

It is certified that error appears in the above-identified patent and that said Letters Patent is hereby corrected as shown below:

Column 6,
Line 43, delete "detector ray" insert therefor -- detector array --.

Column 8,
Line 1, delete "wit" insert therefor -- with --.
Line 9, "power law wing" insert therefor -- power law using --.

Signed and Sealed this

Eighteenth Day of November, 2003

JAMES E. ROGAN
*Director of the United States Patent and Trademark Office*